United States Patent [19]

Büchel et al.

[11] Patent Number: 4,898,875

[45] Date of Patent: * Feb. 6, 1990

[54] MERCAPTO-SUBSTITUTED HYDROXYETHYL-(TRIAZOL-L-YL) DERIVATIVES

[75] Inventors: Karl H. Büchel, Burscheid; Graham Holmwood, Wuppertal; Udo Kraatz, Leverkusen; Wolfgang Krämer, Burscheid; Paul Reinecke, Leverkusen; Wilhelm Brandes, Leichlingen; Wilhelm Stendel, Wuppertal, all of Fed. Rep. of Germany

[73] Assignee: Bayer Aktiengesellschaft, Leverkusen, Fed. Rep. of Germany

[*] Notice: The portion of the term of this patent subsequent to Jun. 6, 2006 has been disclaimed.

[21] Appl. No.: 91,557

[22] Filed: Aug. 31, 1987

[30] Foreign Application Priority Data

Sep. 4, 1986 [DE] Fed. Rep. of Germany ....... 3630129

[51] Int. Cl.$^4$ .................. A01N 43/653; C07D 249/12
[52] U.S. Cl. ..................................... 514/383; 548/262
[58] Field of Search ................ 548/101, 262; 514/184, 514/383

[56] References Cited

U.S. PATENT DOCUMENTS

| | | | |
|---|---|---|---|
| 4,097,599 | 6/1978 | Evans et al. | 548/262 |
| 4,549,900 | 10/1985 | Kramer et al. | 548/262 |
| 4,560,697 | 12/1985 | Richardson et al. | 514/383 |
| 4,584,308 | 4/1986 | Elbe et al. | 514/383 |
| 4,618,619 | 10/1986 | Regel et al. | 514/383 |
| 4,717,734 | 1/1988 | Rogers et al. | 548/262 |
| 4,734,126 | 3/1988 | Holmwood et al. | 71/92 |

FOREIGN PATENT DOCUMENTS 061835 10/1982 European Pat. Off. ............ 548/262
0086173 8/1983 European Pat. Off. .

*Primary Examiner*—Richard L. Raymond
*Assistant Examiner*—Patricia L. Morris

*Attorney, Agent, or Firm*—Sprung Horn Kramer & Woods

[57] ABSTRACT

Novel mercapto-substituted hydroxyethyl-(triazol-1-yl) derivatives of the formula

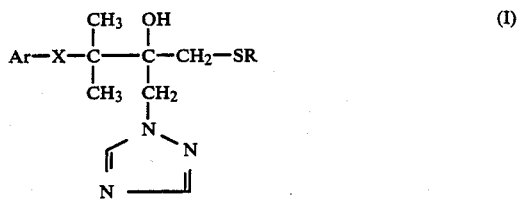

in which Ar represents optionally substituted aryl, X represents oxygen, sulphur, a direct bond or the groupings —CH$_2$—, —CH$_2$—CH$_2$—, —O—CH$_2$—, —SCH$_2$—, —O—CH$_2$—CH$_2$—, and —S—CH$_2$—CH$_2$—, the hetero atom being bonded to the aryl radical if X represents —OCH$_2$—, —SCH$_2$—, —O—CH$_2$—CH$_2$— or —S—CH$_2$—CH$_2$— and R represents hydrogen, optionally substituted alkyl, optionally substituted alkenyl, optionally substituted alkynyl, optionally substituted cycloalkyl, optionally substituted cycloalkylalkyl, optionally substituted aralkyl or optionally substituted phenyl, and their acid addition salts and metal salt complexes are very effective as fungicides and parasiticides. Novel oxiranes of the formula

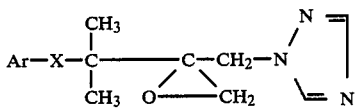

in which Ar and X have the above-mentioned meaning, and their use as intermediates for the synthesis of the mercapto-substituted hydroxyethyl-(triazol-1-yl) derivatives.

10 Claims, No Drawings

MERCAPTO-SUBSTITUTED HYDROXYETHYL-(TRIAZOL-L-YL) DERIVATIVES

The present invention relates to new mercapto-substituted hydroxyethyl-(triazol-1-yl) derivatives, to fungicidal and parasiticidal compositions containing them, and to their use as fungicides and parasiticides.

It has already been disclosed that certain 1-hydroxyalkyl-triazolyl derivatives have fungicidal properties (compare EP-OS (European Published Specification) 0,061,835, EP-OS (European Published Specification) 0,084,834 and EP-OS (European Published Specification) 086,173). Thus, for example, 4-fluoro-2-(4-chlorophenylethyl)-3,3-dimethyl-1-(1,2,4-triazol-1-yl)-butan-2-ol and 4-fluoro-2-(4-chloro-phenyl-thiomethyl)-3,3-dimethyl-1-(1,2,4-triazol-1-yl)-butan-2-ol can be used for combating fungi. However, the activity of these substances is not always completely satisfactory, especially when low amounts are applied and in the case of low concentrations. Their use as parasiticides is also unknown.

The present invention now provides, as new compounds, the mercapto-substituted hydroxyethyl-(triazol-1-yl) derivatives of the formula

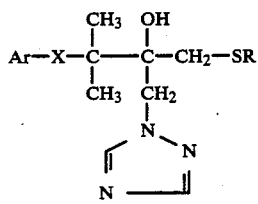

in which

Ar represents optionally substituted aryl,

X represents oxygen, sulphur, a direct bond or the groupings —$CH_2$—, —$CH_2$—$CH_2$—, —O—$CH_2$—, —$SCH_2$—, —O—$CH_2$—$CH_2$— and —S—$CH_2$—$CH_2$—, the hetero atom being bonded to the aryl radical if X represents —$OCH_2$—, —$SCH_2$—, —O—$CH_2$—$CH_2$— or —S—$CH_2$—$CH_2$— and R represents hydrogen, optionally substituted alkyl, optionally substituted alkenyl, optionally substituted alkinyl, optionally substituted cycloalkyl, optionally substituted cycloalkylalkyl, optionally substituted aralkyl or optionally substituted phenyl, and acid addition salts and metal salt complexes thereof.

The new mercapto-substituted hydroxyethyl-(triazol-1-yl) derivatives of the formula (I) have an asymmetrically substituted carbon atom and can therefore be obtained in the two optical isomer forms. The invention relates both to the isomer mixtures and to the individual isomers.

The present invention also provides a process for the preparation of a mercapto-substituted hydroxyethyl-(triazol-1-yl) derivative of the formula (I) and an acid addition salt and metal salt complex thereof, which process comprises reacting an oxirane of the formula

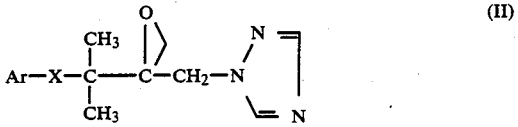

in which

Ar and X have the abovementioned meaning, with a mercaptan of the formula

R—SH (III)

in which

R has the abovementioned meaning, in the presence of a diluent and if appropriate in the presence of an acid-binding agent, and, if appropriate, then adding an acid or a metal salt onto the compounds of the formula (I) thus obtained.

It has furthermore been found that the new mercapto-substituted hydroxyethyl-(triazol-1-yl) derivatives of the formula (I) and acid addition salts and metal salt complexes thereof are distinguished by very good fungicidal and parasiticidal properties.

Surprisingly, the mercapto-substituted hydroxyethyl-(triazol-1-yl) derivatives of the formula (I) according to the invention and acid addition salts and metal salt complexes thereof have a better fungicidal action than 4-fluoro-2-(4-chloro-phenyl-ethyl)-3,3-dimethyl-1-(1,2,4-triazol-1-yl)-butan-2-ol and 4-fluoro-2-(4-chloro-phenyl-thiomethyl)-3,3-dimethyl-1-(1,2,4-triazol-1-yl)-butan-2-ol, which are structurally similar already known active compounds of the same type of action. The mercapto-substituted hydroxyethyl-(triazol-1-yl) derivatives of the formula (I) according to the invention and acid addition salts and metal salt complexes thereof are also distinguished by a good parasiticidal action.

Formula (I) provides a general definition of the mercapto-substituted hydroxyethyl-(triazol-1-yl) derivatives according to the invention. Preferred compounds of the formula (I) are those in which Ar represents aryl which has 6 to 10 carbon atoms and can be monosubstituted or polysubstituted by identical or different substituents from the group comprising halogen, optionally substituted alkyl, optionally substituted alkoxy, optionally substituted alkylthio, optionally substituted alkenyl, optionally substituted alkinyl, optionally substituted phenyl, optionally substituted phenoxy, optionally substituted phenylalkyl, nitro, cyano, formyl, alkylcarbonyl and/or oximes, ketals and hydrazones derived from formyl or alkylcarbonyl, X represents oxygen, sulphur, a direct bond or the groupings —$CH_2$—, —$CH_2$—$CH_2$—, —O—$CH_2$—, —$SCH_2$—, —O—$CH_2$—$CH_2$— and —S—$CH_2$—$CH_2$—, the hetero atom being bonded to the aryl radical if X represents —$OCH_2$—, —$SCH_2$—, —O—$CH_2$—$CH_2$— or —S—$CH_2$—$CH_2$— and R represents hydrogen, optionally substituted straight-chain or branched alkyl with 1 to 12 carbon atoms, optionally substituted alkenyl with 2 to 12 carbon atoms, optionally substituted alkinyl with 3 to 8 carbon atoms, cycloalkyl which has 3 to 6 carbon atoms and is optionally monosubstituted or disubstituted by identical or different substituents from the group comprising halogen and/or alkyl, cycloalkylalkyl which has 3 to 6 carbon atoms in the cycloalkyl part and 1 or 2 carbon atoms in the alkyl part and is optionally monosubstituted or disubstituted by identical or different substituents from the group comprising halogen and/or alkyl, or represents aralkyl with 6 to 10 carbon atoms in the aryl part and 1 to 4 carbon atoms in the alkyl part, it being possible for the aryl part to be monosubstituted or polysubstituted by identical or different substituents from the group comprising halogen, optionally substituted alkyl, optionally substituted alkoxy, optionally substituted alkylthio, optionally substituted alkenyl, optionally substituted alkinyl, optionally substituted phenyl, optionally substituted phenoxy, optionally substituted phenylalkyl, nitro, cyano, formyl, alkylcarbonyl and/or oximes, ketals and hydrazones derived from formyl or alkylcarbonyl, or R represents phenyl which is optionally substituted by halogen and/or alkyl. A particularly preferred group of substances according to the invention are those mercapto-substituted hydroxyethyl-(triazol-1-yl) derivatives of the formula (I)
in which Ar represents phenyl which can be monosubstituted, disubstituted or trisubstituted by identical or different substituents from the group comprising halogen, alkyl with 1 to 4 carbon atoms, halogenoalkyl with 1 or 2 carbon atoms and 1 to 5 halogen atoms, halogenoalkoxy with 1 or 2 carbon atoms and 1 to 5 halogen atoms, halogenoalkylthio with 1 or 2 carbon atoms and 1 to 5 halogen atoms and/or phenyl, X represents oxygen, sulphur, a direct bond or the groupings —CH$_2$— or —CH$_2$—CH$_2$— and R represents hydrogen, optionally substituted straight-chain or branched alkyl with 1 to 12 carbon atoms, optionally substituted alkenyl with 2 to 12 carbon atoms, optionally substituted alkinyl with 3 to 8 carbon atoms, cycloalkyl which has 3 to 6 carbon atoms and is optionally monosubstituted or disubstituted by identical or different substituents from the group comprising halogen and/or alkyl, cycloalkylalkyl which has 3 to 6 carbon atoms in the cycloalkyl part and 1 or 2 carbon atoms in the alkyl part and is optionally monosubstituted or disubstituted by identical or different substituents from the group comprising halogen and/or alkyl, or represents aralkyl which has 6 to 10 carbon atoms in the aryl part and 1 to 4 carbon atoms in the alkyl part, it being possible for the aryl part to be monosubstituted or polysubstituted by identical or different substituents from the group comprising halogen, optionally substituted alkyl, optionally substituted alkoxy, optionally substituted alkylthio, optionally substituted alkenyl, optionally substituted alkinyl, optionally substituted phenyl, optionally substituted phenoxy, optionally substituted phenylalkyl, nitro, cyano, formyl, alkylcarbonyl and/or oximes, ketals and hydrazones derived from formyl or alkylcarbonyl, or R represents phenyl which is mono-, di- or trisubstituted by halogen and/or alkyl with 1 to 4 carbon atoms. Another particularly preferred group of substances according to the invention comprises those mercapto-substituted hydroxyethyl-(triazol-1-yl) derivatives of the formula (I)
in which Ar represents phenyl, which can be monosubstituted, disubstituted or trisubstituted by identical or different substituents from the group comprising halogen, alkyl with 1 to 4 carbon atoms, halogenoalkyl with 1 or 2 carbon atoms and 1 to 5 halogen atoms, halogenoalkoxy with 1 or 2 carbon atoms and 1 to 5 halogen atoms, halogenoalkylthio with 1 or 2 carbon atoms and 1 to 5 halogen atoms, phenyl, formyl and acetyl and/or oxime ethers which are derived from formyl or acetyl, X represents the groupings —O—CH$_2$—, —S—CH$_2$—, —O—CH$_2$—CH$_2$— or —S—CH$_2$—CH$_2$—, the hetero atom in each case being bonded to the phenyl radical, and R represents hydrogen, optionally substituted straight-chain or branched alkyl with 1 to 12 carbon atoms, optionally substituted alkenyl with 2 to 12 carbon atoms, optionally substituted alkinyl with 3 to 8 carbon atoms, cycloalkyl which has 3 to 6 carbon atoms and is optionally monosubstituted or disubstituted by identical or different substituents from the group comprising halogen and/or alkyl, cycloalkylalkyl which has 3 to 6 carbon atoms in the cycloalkyl part and 1 or 2 carbon atoms in the alkyl part and is optionally monosubstituted or disubstituted by identical or different substituents from the group comprising halogen and/or alkyl, or represents aralkyl with 6 to 10 carbon atoms in the aryl part and 1 to 4 carbon atoms in the alkyl part, it being possible for the aryl part to be monosubstituted or polysubstituted by identical or different substituents from the group comprising halogen, optionally substituted alkyl, optionally substituted alkoxy, optionally substituted alkylthio, optionally substituted alkenyl, optionally substituted alkinyl, optionally substituted phenyl, optionally substituted phenoxy, optionally substituted phenylalkyl, nitro, cyano, formyl, alkylcarbonyl and/or oximes, ketals and hydrazones derived from formyl or alkylcarbonyl, or R represents phenyl which is optionally mono-, di- or trisubstituted by halogen and/or alkyl with 1 to 4 carbon atoms. Compounds of the formula (I) which are very especially preferred are those in which Ar represents phenyl which can be monosubstituted, disubstituted or trisubstituted by identical or different substituents from the group comprising fluorine, chlorine, bromine, methyl, ethyl, isopropyl, butyl, trifluoromethyl, trifluoromethoxy, tetrafluoroethoxy, trifluoromethylmercapto, tetrafluoroethylmercapto and/or phenyl, X represents oxygen or the —CH$_2$— group and R represents hydrogen, alkyl which has 1 to 6 carbon atoms and is optionally substituted by halogen, alkenyl which has 2 to 4 carbon atoms and is optionally substituted by halogen, alkinyl which has 3 to 6 carbon atoms and is optionally substituted by halogen, cycloalkyl which has 3 to 6 carbon atoms and is optionally mono- or disubstituted by identical or different substituents from the group comprising fluorine, chlorine and/or methyl, cycloalkylalkyl which has 3 to 6 carbon atoms in the cycloalkyl part and 1 or 2 carbon atoms in the alkyl part and is optionally mono- or disubstituted by identical or different substituents from the group comprising fluorine, chlorine and/or methyl, or represents benzyl, which can be monosubstituted, disubstituted or trisubstituted in the phenyl part by identical or different substituents from the group comprising fluorine, chlorine, bromine, methyl, ethyl, isopropyl, butyl, trifluoromethyl, trifluoromethoxy, tetrafluoroethoxy, trifluoromethylmercapto and/or tetrafluoroethylmercapto, or R represents phenyl which is optionally mono- or disubstituted by fluorine, chlorine and/or methyl. Compounds of the formula (I) which are also very especially preferred are those in which Ar represents phenyl, which can be monosubstituted, disubstituted or trisubstituted by identical or different substituents from the group comprising fluorine, chlorine, bromine, methyl, ethyl, isopropyl, butyl, trifluoromethyl, trifluoromethoxy, tetrafluoroethoxy, trifluoromethylmercapto, tetrafluoroethylmercapto, formyl, acetyl, methoximinomethyl, ethoximinomethyl, methoximinoethyl, ethoximinoethyl and/or phenyl, X represents the groupings —O—CH$_2$—, —S—CH$_2$—, —O—CH$_2$—CH$_2$— or —S—CH$_2$—CH$_2$—, the hetero atom being bonded to the phenyl radical, and R represents hydrogen, alkyl which has 1 to 6 carbon atoms and is optionally substituted by halogen, alkenyl which has 2 to 4 carbon atoms and is optionally substituted by halogen, alkinyl which has 3 to 6 carbon atoms and is optionally substituted by halogen, cycloalkyl which has 3 to 6 carbon atoms and is optionally mono- or disubstituted by identical or different substituents from the group comprising fluorine, chlorine and/or methyl, cycloalkylalkyl which has 3 to 6 carbon atoms in the cycloalkyl part and 1 or 2 carbon atoms in the alkyl part and is optionally mono- or disubstituted by identical or different substituents from the group comprising fluorine, chlorine and/or methyl, or represents benzyl, which can be monosubstituted, disubstituted or trisubstituted in the phenyl part by identical or different substituents from the group comprising fluorine, chlorine, bromine, methyl, ethyl, isopropyl, butyl, trifluoromethyl, trifluoromethoxy, tetrafluoroethoxy, trifluoromethylmercapto and/or tetrafluoroethylmercapto, or R represents phenyl which is optionally mono- or disubstituted by fluorine, chlorine and/or methyl. Compounds of the formula (I) which are furthermore of very special interest are those in which Ar represents phenyl, which can be monosubstituted or disubtituted by identical or different substituents from the group comprising fluorine, chlorine, bromine, methyl, ethyl, isopropyl, butyl, trifluoromethyl, trifluoromethoxy, tetrafluoroethoxy, trifluoromethylmercapto, tetrafluoroethylmercapto, formyl, acetyl, methoximinomethyl, ethoximinomethyl, methoximinoethyl, ethoximinoethyl and/or phenyl, X represents the groupings —O—CH$_2$— or —OCH$_2$—CH$_2$—, the oxygen atom being bonded to the phenyl radical, and R represents hydrogen, methyl, ethyl, isopropyl, n-propyl, n-butyl, iso-butyl, tert.-butyl, n-hexyl, allyl, propinyl, cyclohexyl, dichlorocyclopropyl, dichlorocyclopropyl-methyl, methylcyclohexyl, 4-chlorobenzyl or 4-chlorophenyl. Finally, compounds of the formula (I) which are also of very special interest are those in which Ar represents phenyl, which can be monosubstituted or disubstituted by identical or different substituents from the group comprising fluorine, chlorine, bromine, methyl, ethyl, isopropyl, butyl, trifluoromethyl, trifluoromethoxy, tetrafluoroethoxy, trifluoromethylmercapto, tetrafluoroethylmercapto and/or phenyl, X represents oxygen or the grouping —CH$_2$— and R represents hydrogen, methyl, ethyl, isopropyl, n-propyl, n-butyl, iso-butyl, tert.-butyl, n-hexyl, allyl, propinyl, cyclohexyl, dichlorocyclopropyl, dichlorocyclopropylmethyl, methylcyclohexyl, 4-chlorobenyl or 4-chlorophenyl. Addition products of acids and those mercaptosubstituted hydroxyethyl-(triazol-1-yl) derivatives of the formula (I) in which Ar, X and R have those meanings which have already been mentioned as preferred for these substituents in connection with the description of the substances according to the invention are also preferred compounds according to the invention.

The acids which can be added include, preferably, hydrogen halide acids, such as, for example, hydrochloric acid and hydrobromic acid, in particular hydrochloric acid, and furthermore phosphoric acid, nitric acid, mono- and bifunctional carboxylic acids and hydroxycarboxylic acids, such as, for example, acetic acid, maleic acid, succinic acid, fumaric acid, tartaric acid, citric acid, salicylic acid, sorbic acid and lactic acid, and sulphonic acids, such as, for example, p-toluenesulphonic acid and 1,5-naphthalenedisulphonic acid.

Compounds according to the invention which are also preferred are addition products of salts of metals of main groups II to IV and of subgroups I and II and IV to VIII of the periodic table of the elements and those mercapto-substituted hydroxyethyl-(triazol-1-yl) derivatives of the formula (I) in which Ar, X and R have the meanings which have already been given as preferred for these substituents.

Salts of copper, zinc, manganese, magnesium, tin, iron and nickel are particularly preferred here. Possible anions of these salts are those which are derived from those acids which lead to physiologically acceptable addition products. Particularly preferred acids of this type are, in this connection, the hydrogen halide acids, such as, for example, hydrochloric acid and hydrobromic acid, and furthermore phosphoric acid, nitric acid and sulphuric acid.

If, for example, 2-(4-chlorophenoxy-tert.-butyl)-2-(1,2,4-triazol-1-yl-methyl)-oxirane and methylmercaptan are used as starting substances, the course of the process according to the invention can be represented by the following equation:

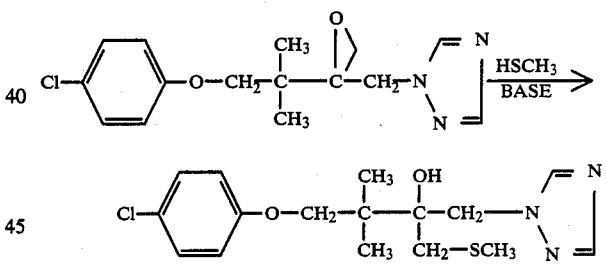

Formula (II) provides a general definition of the oxiranes required as starting substances in the process according to the invention. In this formula, Ar and X preferably have those meanings which have already been mentioned as preferred for these radicals in connection with the description of the substances of the formula (1) according to the invention.

The oxiranes of the formula (II) are new. They can be prepared by a process in which ketones of the formula

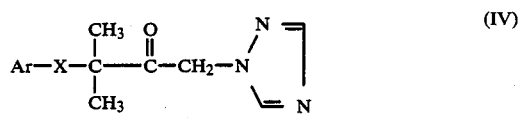

in which

Ar and X have the abovementioned meaning, either
(α) are reacted with dimethyloxosulphonium methylide of the formula

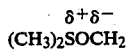

(V)

in the presence of a diluent, such as, for example, dimethylsulphoxide, at temperatures between 20° C. and 80° C., or (β) are reacted with trimethylsulphonium methylsulphate of the formula

(VI)

in the presence of an inert organic solvent, such as, for example, acetonitrile, and in the presence of a base, such as, for example, sodium methylate, at temperatures between 0° C. and 60° C., preferably at room temperature.

If appropriate, the oxiranes of the formula (II) can be further reacted directly in the process according to the invention, without isolation.

The ketones of the formula (IV) required as starting substances in the preparation of the oxiranes of the formula (II) by the above processes are known or can be prepared in a simple manner by methods which are known in principle (compare EP-OS (European Published Specification) 0,054,865 and DE-OS (German Published Specification) 3,222,220).

Formula (III) provides a general definition of the mercaptans also required as starting substances for the process according to the invention.

In this formula, R preferably has the meanings which have already been mentioned as preferred for R in connection with the description of the substances of the formula (I) according to the invention.

The mercaptans of the formula (III) are generally known compounds of organic chemistry.

Possible diluents for the process according to the invention for the preparation of mercapto-substituted hydroxyethyl-(triazol-1-yl) derivatives of the formula (I) are all the inert organic solvents. Solvents which can preferably be used are alcohols, such as ethanol and methoxyethanol; ketones, such as, for example, 2-butanone; nitriles, such as, for example, acetonitrile; esters, such as, for example, ethyl acetate; ethers, such as, for example, dioxane; aromatic hydrocarbons, such as, for example, benzene and toluene; or amides, such as, for example, dimethylformamide.

Possible acid-binding agents for the reaction according to the invention are all the inorganic and organic bases which can usually be employed. These include, preferably, alkali metal carbonates, such as, for example, sodium and potassium carbonate; alkali metal hydroxides, such as, for example, sodium hydroxide; alkali metal alcoholates, such as, for example, sodium and potassium methylate and ethylate; alkali metal hydrides, such as, for example, sodium hydride; and lower tertiary alkylamines, cycloalkylamines and aralkylamines, such as, in particular, triethylamine.

The reaction temperatures can be varied within a substantial range in carrying out the process according to the invention. The reaction is in general carried out at temperatures between 0° and 200° C., preferably between 60° and 150° C.

In carrying out the process according to the invention, preferably 1 to 2 mol of mercaptan of the formula (III) and if appropriate 1 to 2 mol of acid-binding agent are employed per mol of oxirane of the formula (II).

The end products are isolated in the generally customary manner.

The compounds of the formula (I) obtainable by the process according to the invention can be converted into acid addition salts or metal salt complexes.

Those acids which have already been mentioned as preferred acids in connection with the description of the acid addition salts according to the invention are preferably suitable for the preparation of acid addition salts of the compounds of the formula (I).

The acid addition salts of the compounds of the formula (I) can be obtained in a simple manner by customary salt formation methods, for example by dissolving a compound of the general formula (I) in a suitable inert solvent and adding the acid, for example hydrochloric acid, and they can be isolated in a known manner, for example by filtration, and if appropriate purified by washing with an inert organic solvent.

Those salts of metals which have already been described above are preferably suitable for the preparation of metal salt complexes of the compounds of the general formula (I).

The metal salt complexes of compounds of the general formula (I) can be obtained in a simple manner by customary processes, thus, for example, by dissolving the metal salt in alcohol, for example ethanol, and adding the solution to compounds of the general formula (I). Metal salt complexes can be purified in a known manner, for example by filtration, isolation and, if appropriate, by recrystallization.

The active compounds according to the invention exhibit a powerful microbicidal action and can be used as fungicides.

Fungicidal agents are employed in plant protection for combating Plasmodiophoromycetes, Oomycetes, Chytridiomycetes, Zygomycetes, Ascomycetes, Basidiomycetes and Deuteromycetes.

Some causative organisms of fungal and bacterial diseases which come under the generic names listed above may be mentioned as examples, but not by way of limitation: Xanthomonas species, such as Xanthomonas oryzae; Pseudomonas species, such as Pseudomonas lachrymans; Erwinia species, such as Erwinia amylovora; Pythium species, such as Pythium ultimum; Phytophthoraspecies, such as Phytophthora infestans; Pseudoperonospora species, such as Pseudoperonospora humuli or Pseudoperonospora cubense; Plasmopara species, such as Plasmopara viticola; Peronospora species, such as Peronospora pisi or P.brassicae; Erysiphe species, such as Erysiphe graminis; Sphaerotheca species, such as, Sphaerotheca fuliginea; Podosphaera species, such as Podosphaera leucotricha; Venturia species, such as Venturia inaequalis; Pyrenophora species, such as Pyrenophora teres or P. graminea (conidia form: Drechslera, syn: Helminthosporium); Cochliobolus species, such as Cochliobolus sativus (conidia form: Drechslera, syn: Helminthosporium); Uromyces species, such as Uromyces appendiculatus; Puccinia species, such Puccinia recondita; Tilletia species, such as Tilletia caries; Ustilago species, such as Ustilago nudaor Ustilago avenae; Pellicularia species, such as Pellicularia sasakii; Pyricularia species, such as Pyricularia oryzae; Fusarium species, such as Fusariu culmorum; Botrytis species, such as Botrytis cinerea; Septoria species, such as Septoria nodorum; Leptosphaeria species, such as Leptosphaeria nodorum; Cercospora species, such as Cercospora canescens; Alternaria species, such as Alternaria brassicae and Pseudocercosporella species, such as Pseudocercosporella herpotrichoides.

The good toleration, by plants, of the active compounds, at the concentrations required for combating plant diseases, permits treatment of above-ground parts of plants, of vegetative propagation stock and seeds, and of the soil. The active compounds according to the invention can be used with particularly good success protectively against Leptosphaeria nodorum on wheat and Botrytis on beans and as seed treatment agents on wheat against Fusarium culmorum.

It should be emphasized that the substances according to the invention can be used not only protectively but also systemically for combating mildew and Pyrenophora teres on cereals and against Pyricularia oryzae on rice.

The active compounds according to the invention also have plant growth-regulating properties.

The active compounds according to the invention moreover have a parasiticidal activity and are suitable for combating insects, mites, ticks and the like in the field of livestock husbandry and animal breeding, it being possible to achieve better results, for example higher milk yields, a heavier weight, a more attractive animal coat or a longer life and the like, by combating the pests.

The active compounds according to the invention are used in this field in a known manner, such as by external application in the form, for example, of dips, sprays, pour-on and spot-on formulations and powders.

The active compounds are particularly suitable for combating ectoparasites, such as, for example, Psoroptes ovis and Boophilus microplus.

The active compounds can be converted to the customary formulations, such as solutions, emulsions, suspensions, powders, foams, pastes, granules, aerosols, very fine capsules in polymeric substances and in coating compositions for seed, as well as ULV formulations.

These formulations are produced in known manner, for example by mixing the active compounds with extenders, that is, liquid solvents, liquefied gases under pressure, and/or solid carriers, optionally with the use of surface-active agents, that is, emulsifying agents and/or dispersing agents, and/or foam-forming agents. In the case of the use of water as an extender, organic solvents can, for example, also be used as auxiliary solvents. As liquid solvents, there are suitable in the main: aromatics, such as xylene, toluene or alkyl naphthalenes, chlorinated aromatics or chlorinated aliphatic hydrocarbons, such as chlorobenzenes, chloroethylenes or methylene chloride, aliphatic hydrocarbons, such as cyclohexane or paraffins, for example mineral oil fractions, alcohols, such as butanol or glycol as well as their ethers and esters, ketones, such as acetone, methyl ethyl ketone, methyl isobutyl ketone or cyclohexanone, strongly polar solvents, such as dimethylformamide and dimethylsulphoxide, as well as water. By liquefied gaseous extenders or carriers are meant liquids which are gaseous at normal temperature and under normal pressure, for example aerosol propellants, such as halogenated hydrocarbons as well as butane, propane, nitrogen and carbon dioxide. As solid carriers there are suitable: for example ground natural minerals, such as kaolins, clays, talc, chalk, quartz, attapulgite, montmorillonite or diatomaceous earth, and ground synthetic minerals, such as highly-dispersed silicic acid, alumina and silicates. As solid carriers for granules there are suitable: for example crushed and fractionated natural rocks such as calcite, marble, pumice, sepiolite and dolomite, as well as synthetic granules of inorganic and organic meals, and granules of organic material such as sawdust, coconut shells, maize cobs and tobacco stalks. As emulsifying and/or foam-forming agents there are suitable: for example non-ionic and anionic emulsifiers, such as polyoxyethylene-fatty acid esters, polyoxyethylene-fatty alcohol ethers, for example alkylaryl polyglycol ethers, alkyl sulphonates, alkyl sulphates, aryl sulphonates as well as albumin hydrolysation products. As dispersing agents there are suitable: for example ligninsulphite waste liquors and methylcellulose.

Adhesives such as carboxymethylcellulose and natural and synthetic polymers in the form of powders, granules or latices, such as gum arabic, polyvinyl alcohol and polyvinyl acetate, as well as natural phospholipids, such as cephalins and lecithins, and synthetic phospholipids, can be used in the formulations. Other additives can be mineral and vegetable oils.

It is possible to use colorants such as inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

The formulations in general contain between 0.1 and 95 percent by weight of active compound, preferably between 0.5 and 90%.

The active compounds according to the invention can be present in the formulations as a mixture with other known active compounds, such as fungicides, insecticides, acaricides and herbicides, as well as in mixtures with fertilizers and other growth regulators.

The active compounds can be used as such or in the form of their formulations or the use forms prepared therefrom, such as ready-to-use solutions, emulsifiable concentrates, emulsions, foams, suspensions, wettable powders, pastes, soluble powders, dusts and granules. They are used in the customary manner, for example by watering, spraying, atomizing, scattering, dusting, foaming, brushing on and the like. It is furthermore possible to apply the active compounds by the ultra-low volume method or to inject the active compound formulation or the active compound itself into the soil. The seeds of the plants can also be treated.

In the treatment of parts of plants, the active compound concentrations in the use forms can be varied within a substantial range. They are, in general, between 1 and 0.0001% by weight, preferably between 0.5 and 0.001%.

In the treatment of seed, amounts of active compound of 0.001 to 50 g per kilogram of seed, preferably 0.01 to 10 g, are generally required.

For the treatment of soil, active compound concentrations of 0.00001 to 0.1% by weight, preferably 0.0001 to 0.02%, are required at the place of action.

The present invention also provides a fungicidal and parasiticidal composition containing as active ingredient a compound of the formula (I) according to the present invention in admixture with a solid diluent or carrier or in admixture with a liquid diluent or carrier containing a surface-active agent.

The present invention also provides a method of combating fungi and parasites which comprises applying to the fungi and parasites or to a habitat thereof, a compound of the formula (I) according to the present invention alone or in the form of a composition containing as active ingredient a compound of the formula (I)

according to the present invention in admixture with a diluent or carrier.

The preparation and use of the active compounds according to the invention can be seen from the following examples.

PREPARATION EXAMPLES

Example 1

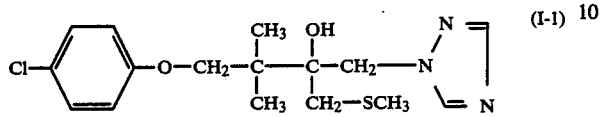

1.8 g of sodium hydroxide in 80 ml of ethanol are added to 18 g (0.042 mol) of 2-(4-chloro-phenoxy-tert.-butyl)-2-(1,2,4-triazol-1-yl-methyl)-oxirane in 80 ml of ethanol, with stirring. The mixture is cooled and 2.4 g (0.055 mol) of methylmercaptan are passed in at −15° C. The reaction mixture is then allowed to come slowly to room temperature and is stirred for a further 16 hours. The mixture is concentrated, the oil which remains is taken up in 350 ml of dichloromethane and the mixture is washed twice with 500 ml of water, dried over sodium sulphate and concentrated. The residue is purified over a silica gel column (mobile phase: cyclohexane/ethyl acetate 1:1).

12 g (80% of theory) of 2-(methylthiomethyl)-3,3-dimethyl-4-(4-chloro-phenoxy)-1-(1,2,4-triazol-1-yl)-butan-2-ol are obtained as a viscous oil. The structure of the compound is proved by the nuclear magnetic resonance spectrum.

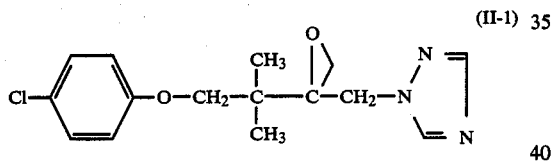

154 g (0.7 mol) of trimethylsulphoxonium iodide are added to a solution of 170 ml of absolute dimethylsulphoxide and 78.4 g of potassium tert.-butylate. The mixture is stirred for 5 hours, 182 g (0.7 mol) of 1-(1,2,4-triazol-1-yl)-4-(4-chloro-phenoxy)-3,3-dimethyl-butan-2-one are then added dropwise and the mixture is stirred at 45° C. for 16 hours. After addition of 300 ml of water, the organic phase is separated off and the aqueous phase is extracted once with 500 ml of dichloromethane. The organic phases are combined and washed twice with 1,200 ml of water. After drying over sodium sulphate, the diluent is stripped off and the residue is degassed under a high vacuum.

187 g (86.8% of theory) of 2-(4-chloro-phenoxy-tert.-butyl)-2-(1,2,4-triazol-1-yl-methyl)-oxirane are obtained as an oil.

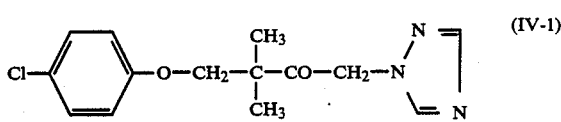

222 g (0.73 mol) of 1-bromo-4-(4-chloro-phenoxy)-3,3-dimethyl-butan-2-one, dissolved in acetone, are added dropwise to a mixture of 138 g (1 mol) of potassium carbonate and 50.4 g (0.73 mol) of 1,2,4-triazole in 800 ml of absolute boiling acetone, with stirring.

The mixture is warmed under reflux for 5 hours and cooled to 0° to 10° C., the salt is filtered off and the filtrate is concentrated under reduced pressure. The residue is taken up in 800 ml of dichloromethane and washed twice with 1,300 ml of water. The organic phase is dried over sodium sulphate and concentrated.

182 g (85% of theory) of 1-(1,2,4-triazol-1-yl)-4-(4-chloro-phenoxy)-3,3-dimethylbutan-2-one are obtained in the form of colourless crystals of melting point 88°–90° C.

The compounds of the formula

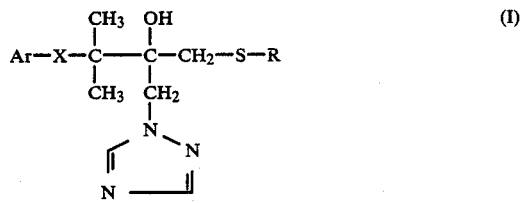

listed below are obtained in a manner analogous to the method described in Example 1, taking into consideration the statements on the process according to the invention:

TABLE 1

| Ex. No. | Comp. No. | Ar | X | R | Melting point (°C.) or refractive index $[n_D^{20}]$ |
|---|---|---|---|---|---|
| 2 | I-2 | F-⟨phenyl⟩- | —CH₂ | C₂H₅ | Oil |
| 3 | I-3 | 2,6-Cl₂-⟨phenyl⟩- | —O—CH₂ | nC₃H₇ | Oil |

TABLE 1-continued

| Ex. No. | Comp. No. | Ar | X | R | Melting point (°C.) or refractive index $[n_D^{20}]$ |
|---|---|---|---|---|---|
| 4 | I-4 | 3,4-dichlorophenyl | —O—CH$_2$ | C$_2$H$_5$ | 85 |
| 5 | I-5 | 3,4-dichlorophenyl | —O—CH$_2$ | iC$_3$H$_7$ | 94–97 |
| 6 | I-6 | 3,4-dichlorophenyl | —O—CH$_2$ | —CH$_2$-(4-chlorophenyl) | 92–94 |
| 7 | I-7 | 2-methyl-4-chlorophenyl | —O—CH$_2$ | C$_2$H$_5$ | Oil |
| 8 | I-8 | 2-methyl-4-chlorophenyl | —O—CH$_2$ | nC$_4$H$_9$ | Oil |
| 9 | I-9 | 2,6-dichlorophenyl | —O—CH$_2$ | nC$_4$H$_9$ | Oil |
| 10 | I-10 | 3,4-dichlorophenyl | —O—CH$_2$ | nC$_3$H$_7$ | 71–73 |
| 11 | I-11 | 3,4-dichlorophenyl | —O—CH$_2$ | nC$_4$H$_9$ | Oil |
| 12 | I-12 | 2-methyl-4-chlorophenyl | —O—CH$_2$ | nC$_3$H$_7$ | Oil |

TABLE 1-continued
| Ex. No. | Comp. No. | Ar | X | R | Melting point (°C.) or refractive index [$n_D^{20}$] |
|---|---|---|---|---|---|
| 13 | I-13 | 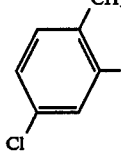 | —O—CH$_2$ | iC$_3$H$_7$ | 86–99 |
| 14 | I-14 | 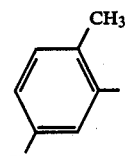 | —O—CH$_2$ | 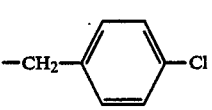 | Oil |
| 15 | I-15 | 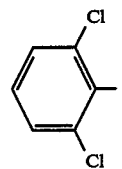 | —O—CH$_2$ | C$_2$H$_5$ | Oil |
| 16 | I-16 | 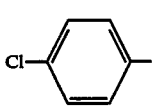 | —O—CH$_2$ | 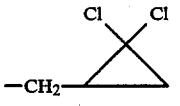 | Oil |
| 17 | I-17 | 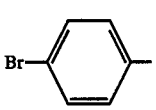 | —O—CH$_2$ | 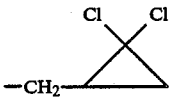 | Oil |
| 18 | I-18 |  | —O—CH$_2$ | 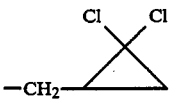 | Oil |
| 19 | I-19 | 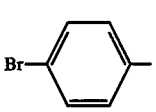 | —O—CH$_2$ | C$_2$H$_5$ | Oil |
| 20 | I-20 | 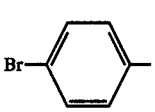 | —O—CH$_2$ | nC$_3$H$_7$ | Oil |
| 21 | I-21 | 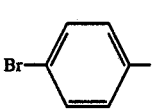 | —O—CH$_2$ | iC$_3$H$_7$ | Oil |
| 22 | I-22 | 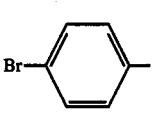 | —O—CH$_2$ | nC$_4$H$_9$ | Oil |
| 23 | I-23 | 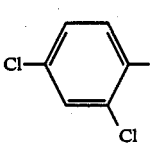 | —O—CH$_2$ | C$_2$H$_5$ | Oil |

TABLE 1-continued

| Ex. No. | Comp. No. | Ar | X | R | Melting point (°C.) or refractive index [$n_D^{20}$] |
|---|---|---|---|---|---|
| 24 | I-24 | 2,4-dichlorophenyl | —O—CH$_2$ | nC$_3$H$_7$ | Oil |
| 25 | I-25 | 2,4-dichlorophenyl | —O—CH$_2$ | nC$_4$H$_9$ | Oil |
| 26 | I-26 | 4-fluorophenyl | —CH$_2$ | —CH$_2$—C(Cl)(Cl) (cyclopropyl with 2,2-diCl) | Oil |
| 27 | I-27 | 2,4-dichlorophenyl | —O—CH$_2$ | iC$_3$H$_7$ | Oil |
| 28 | I-28 | biphenyl-4-yl | —O—CH$_2$ | C$_2$H$_5$ | Oil |
| 29 | I-29 | 4-bromophenyl | —O—CH$_2$ | CH$_3$ | 69–71 |
| 30 | I-30 | biphenyl-4-yl | —O—CH$_2$ | CH$_3$ | 120–123 |
| 31 | I-31 | 4-fluorophenyl | —CH$_2$ | CH$_3$ | 135 |
| 32 | I-32 | 2,4-dichlorophenyl | —O—CH$_2$ | CH$_3$ | Oil |
| 33 | I-33 | biphenyl-4-yl | —O—CH$_2$ | nC$_4$H$_9$ | Oil |
| 34 | I-34 | biphenyl-4-yl | —O—CH$_2$ | nC$_3$H$_7$ | Oil |
| 35 | I-35 | biphenyl-4-yl | O—CH$_2$ | iC$_3$H$_7$ | Oil |

TABLE 1-continued

| Ex. No. | Comp. No. | Ar | X | R | Melting point (°C.) or refractive index [$n_D^{20}$] |
|---|---|---|---|---|---|
| 36 | I-36 | 4-Br-C$_6$H$_4$- | —CH$_2$ | —CH$_2$—CH=CH$_2$ | 108 |
| 37 | I-37 | 2-Cl-C$_6$H$_4$- | —CH$_2$ | iC$_3$H$_7$ | Oil |
| 38 | I-38 | 2-Cl-C$_6$H$_4$- | —CH$_2$ | —CH$_2$—CH=CH$_2$ | Oil |
| 39 | I-39 | 2-Cl-C$_6$H$_4$- | —CH$_2$ | C$_2$H$_5$ | Oil |
| 40 | I-40 | 4-Br-C$_6$H$_4$- | —CH$_2$ | iC$_3$H$_7$ | 80–81 |
| 41 | I-41 | 4-Cl-C$_6$H$_4$- | —CH$_2$ | nC$_3$H$_7$ | Oil |
| 42 | I-42 | 4-Cl-C$_6$H$_4$- | —CH$_2$ | CH$_3$ | 146 |
| 43 | I-43 | 4-Cl-C$_6$H$_4$- | —CH$_2$ | iC$_4$H$_9$ | Oil |
| 44 | I-44 | 4-Cl-C$_6$H$_4$- | —CH$_2$ | —CH$_2$—CH=CH$_2$ | Oil |
| 45 | I-45 | 4-Cl-C$_6$H$_4$- | CH$_2$ | C$_2$H$_5$ | 82–83 |
| 46 | I-46 | 4-Cl-C$_6$H$_4$- | CH$_2$ | iC$_3$H$_7$ | resin |
| 47 | I-47 | 4-Cl-C$_6$H$_4$- | CH$_2$ | nC$_4$H$_9$ | resin |

TABLE 1-continued

| Ex. No. | Comp. No. | Ar | X | R | Melting point (°C.) or refractive index [$n_D^{20}$] |
|---|---|---|---|---|---|
| 48 | I-48 | 4-Cl-C$_6$H$_4$- | CH$_2$ | nC$_6$H$_{13}$ | resin |
| 49 | I-49 | 4-CH$_3$-C$_6$H$_4$- | CH$_2$ | nC$_3$H$_7$ | Oil |
| 50 | I-50 | 4-CH$_3$-C$_6$H$_4$- | CH$_2$ | C$_2$H$_5$ | 102–103 |
| 51 | I-51 | 4-CF$_3$O-C$_6$H$_4$- | CH$_2$ | nC$_3$H$_7$ | oil |
| 52 | I-52 | 4-CF$_3$O-C$_6$H$_4$- | CH$_2$ | C$_2$H$_5$ | Oil |
| 53 | I-53 | 4-F-C$_6$H$_4$- | CH$_2$ | nC$_3$H$_7$ | Oil |
| 54 | I-54 | 4-F-C$_6$H$_4$- | CH$_2$ | nC$_4$H$_9$ | Oil |
| 55 | I-55 | 4-F-C$_6$H$_4$- | CH$_2$ | iC$_3$H$_7$ | 76 |
| 56 | I-56 | 4-F-C$_6$H$_4$- | CH$_2$ | H | Oil |
| 57 | I-57 | 4-F-C$_6$H$_4$- | CH$_2$ | nC$_6$H$_{13}$ | Oil |
| 58 | I-58 | 4-F-C$_6$H$_4$- | CH$_2$ | -CH$_2$-C$_6$H$_4$-4-Cl | Oil |
| 59 | I-59 | 4-F$_3$CS-C$_6$H$_4$- | CH$_2$ | C$_2$H$_5$ | Oil |
| 60 | I-60 | 4-F$_3$CS-C$_6$H$_4$- | CH$_2$ | nC$_3$H$_7$ | Oil |

TABLE 1-continued

| Ex. No. | Comp. No. | Ar | X | R | Melting point (°C.) or refractive index [$n_D^{20}$] |
|---|---|---|---|---|---|
| 61 | I-61 | 4-F₃CS-C₆H₄- | CH₂ | nC₄H₉ | Oil |
| 62 | I-62 | 4-F₃CS-C₆H₄- | CH₂ | iC₃H₇ | Oil |
| 63 | I-63 | 4-F₃CS-C₆H₄- | CH₂ | H | Oil |
| 64 | I-64 | 3-CH₃-C₆H₄- | CH₂ | C₂H₅ | 78 |
| 65 | I-65 | 3-H₃C-C₆H₄- | CH₂ | iC₃H₇ | Oil |
| 66 | I-66 | 3-H₃C-C₆H₄- | CH₂ | nC₄H₉ | Oil |
| 67 | I-67 | 2-CH₃-C₆H₄- | CH₂ | C₂H₅ | Oil |
| 68 | I-68 | 4-Cl-C₆H₄- | OCH₂ | C₂H₅ | Oil |
| 69 | I-69 | 2-H₃C-4-Cl-C₆H₃- | OCH₂ | C₂H₅ | Oil |
| 70 | I-70 | 2-H₃C-4-Cl-C₆H₃- | OCH₂ | nC₃H₇ | Oil |
| 71 | I-71 | 3-Cl-5-H₃C-C₆H₃- | OCH₂ | nC₄H₉ | Oil |

TABLE 1-continued

| Ex. No. | Comp. No. | Ar | X | R | Melting point (°C.) or refractive index [$n_D^{20}$] |
|---|---|---|---|---|---|
| 72 | I-72 | 2-CH$_3$-C$_6$H$_4$ | CH$_2$ | nC$_3$H$_7$ | Oil |
| 73 | I-73 | 2-CH$_3$-C$_6$H$_4$ | CH$_2$ | iC$_3$H$_7$ | Oil |
| 74 | I-74 | 2-CH$_3$-C$_6$H$_4$ | CH$_2$ | nC$_4$H$_9$ | Oil |
| 75 | I-75 | 2-CH$_3$-C$_6$H$_4$ | CH$_2$ | —CH$_2$—C$_6$H$_4$—4-Cl | Oil |
| 76 | I-76 | 4-Cl-3-CF$_3$-C$_6$H$_3$ | CH$_2$ | nC$_4$H$_9$ | Oil |
| 77 | I-77 | 4-Cl-3-CF$_3$-C$_6$H$_3$ | CH$_2$ | C$_2$H$_5$ | Oil |
| 78 | I-78 | 3,4-Cl$_2$-C$_6$H$_3$ | CH$_2$ | C$_2$H$_5$ | Oil |
| 79 | I-79 | 3,4-Cl$_2$-C$_6$H$_3$ | CH$_2$ | nC$_3$H$_7$ | Oil |
| 80 | I-80 | 3,4-Cl$_2$-C$_6$H$_3$ | CH$_2$ | iC$_3$H$_7$ | Oil |
| 81 | I-81 | 3,4-Cl$_2$-C$_6$H$_3$ | CH$_2$ | nC$_4$H$_9$ | Oil |

TABLE 1-continued

| Ex. No. | Comp. No. | Ar | X | R | Melting point (°C.) or refractive index [$n_D^{20}$] |
|---|---|---|---|---|---|
| 82 | I-82 | 3,4-di-Cl-phenyl | CH$_2$ | —CH$_2$—(4-Cl-phenyl) | Oil |
| 83 | I-83 | 3-Cl-4-CF$_3$-phenyl | CH$_2$ | iC$_3$H$_7$ | Oil |
| 84 | I-84 | 3-Cl-4-CF$_3$-phenyl | CH$_2$ | nC$_3$H$_7$ | Oil |
| 85 | I-85 | 4-Cl-phenyl | OCH$_2$ | nC$_3$H$_7$ | Oil |
| 86 | I-86 | 4-Cl-phenyl | OCH$_2$ | iC$_3$H$_7$ | Oil |
| 87 | I-87 | 4-Cl-phenyl | OCH$_2$ | nC$_4$H$_9$ | Oil |
| 88 | I-88 | 4-Cl-phenyl | OCH$_2$ | nC$_6$H$_{13}$ | Oil |
| 89 | I-89 | 4-Cl-phenyl | OCH$_2$—CH$_2$ | nC$_3$H$_7$ | Oil |
| 90 | I-90 | 4-Cl-phenyl | OCH$_2$—CH$_2$ | iC$_3$H$_7$ | Oil |
| 91 | I-91 | 4-Cl-phenyl | OCH$_2$—CH$_2$ | C$_2$H$_5$ | Oil |
| 92 | I-92 | 4-Cl-phenyl | OCH$_2$—CH$_2$ | —CH$_2$—CH=CH$_2$ | Oil |
| 93 | I-93 | biphenyl-4-yl | O | 4-Cl-phenyl | Resin |

TABLE 1-continued

| Ex. No. | Comp. No. | Ar | X | R | Melting point (°C.) or refractive index [$n_D^{20}$] |
|---|---|---|---|---|---|
| 94 | I-94 | 4-Cl, 2-CH₃-phenyl | O | 4-Cl-phenyl | Resin |
| 95 | I-95 | 4-Cl-phenyl | O | C₂H₅ | 65 |
| 96 | I-96 | 4-Cl-phenyl | O | cyclohexyl (H) | 1.5405 |
| 97 | I-97 | 4-Cl-phenyl | O | nC₃H₇ | 1.5398 |
| 98 | I-98 | 4-Cl-phenyl | O | iC₃H₇ | 1.5320 |
| 99 | I-99 | 4-Cl-phenyl | O | nC₆H₁₃ | Oil |

The oxiranes of the formula

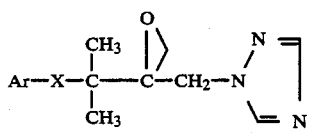

(II)

Listed in the following Table 2 are also prepared by the method described in Example 1.

TABLE 2

| Ex. No. | Comp. No. | Ar | X | Melting point [°C.] or refractive index [$n_D^{20}$] |
|---|---|---|---|---|
| 100 | II-2 | 4-F-phenyl | —CH₂ | Oil |
| 101 | II-3 | 2,6-Cl₂-phenyl | —OCH₂ | Oil |
| 102 | II-4 | 3,4-Cl₂-phenyl | —OCH₂ | Oil |
| 103 | II-5 | 4-Cl, 2-CH₃-phenyl | —OCH₂ | Oil |
| 104 | II-6 | 4-Br-phenyl | —OCH₂ | Oil |
| 105 | II-7 | biphenyl | —OCH₂ | Oil |
| 106 | II-8 | 3,4-Cl₂-phenyl | —OCH₂ | Oil |
| 107 | II-9 | 4-Br-phenyl | CH₂ | Oil |
| 108 | II-10 | 4-Cl-phenyl | —CH₂— | Oil |
| 109 | II-11 | 2-Cl-phenyl | —CH₂— | Oil |

TABLE 2-continued

| Ex. No. | Comp. No. | Ar | X | Melting point [°C.] or refractive index [$n_D^{20}$] |
|---|---|---|---|---|
| 110 | II-12 | 4-CH₃-C₆H₄- | —CH₂— | Oil |
| 111 | II-13 | 4-CF₃O-C₆H₄- | —CH₂— | Oil |
| 112 | II-14 | 4-F₃CS-C₆H₄- | —CH₂— | Oil |
| 113 | II-15 | 3-CH₃-C₆H₄- | —CH₂— | Oil |
| 114 | II-16 | 2-CH₃-C₆H₄- | —CH₂— | Oil |
| 115 | II-17 | 3-CH₃-4-Cl-C₆H₃- | —OCH₂ | Oil |
| 116 | II-18 | 4-Cl-3-CF₃-C₆H₃- | —CH₂— | Oil |
| 117 | II-19 | 3,4-Cl₂-C₆H₃- | —CH₂— | Oil |
| 118 | II-20 | 4-Cl-C₆H₄- | —OCH₂CH₂ | Oil |
| 119 | II-21 | 4-C₆H₅-C₆H₄- | O | Oil |
| 120 | II-22 | 3-CH₃-4-Cl-C₆H₃- | O | Oil |
| 121 | II-23 | 4-Cl-C₆H₄- | O | Oil |
| 122 | II-24 | 4-Cl-C₆H₄- | O | Oil |

The compounds of the formula

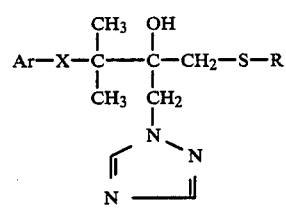

shown below are obtained in a manner analogous to the method described in Example 1, taking into consideration the statements on the process according to the invention:

TABLE 3

| Ex. No. | Comp. No. | Ar | X | R | Melting point [°C.] or refractive index [$n_D^{20}$] |
|---|---|---|---|---|---|
| 123 | I-100 | 4-F-C₆H₄- | —CH₂ | —CH₂—CH=CH₂ | 74–76 |
| 124 | I-101 | 4-Br-C₆H₄- | —OCH₂— | —CH₂—CH=CH₂ | Oil |
| 125 | I-102 | 4-C₆H₅-C₆H₄- | —O—CH₂— | —CH₂—CH=CH₂ | Oil |
| 126 | I-103 | 3,4-Cl₂-C₆H₃- | —O—CH₂— | —CH₂—CH=CH₂ | Oil |
| 127 | I-104 | 4-Cl-C₆H₄- | —O—CH₂— | —CH₂—CH=CH₂ | Oil |
| 128 | I-105 | 3,4-Cl₂-C₆H₃- | —O—CH₂— | —CH₂—CH=CH₂ | Oil |

TABLE 3-continued

| Ex. No. | Comp. No. | Ar | X | R | Melting point [°C.] or refractive index [$n_D^{20}$] |
|---|---|---|---|---|---|
| 129 | I-106 |  | —CH$_2$— | —CH$_2$—CH=CH$_2$ | 66–68 |
| 130 | I-107 |  | —O— | n-C$_4$H$_9$ | 1,5349 |
| 131 | I-108 |  | —O— | i-C$_4$H$_9$ | 1,5310 |

Use Examples:

The substances shown below are employed as comparison compounds in the use examples which follow.

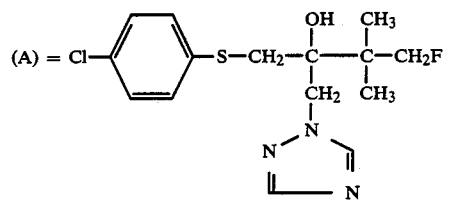

(A) =

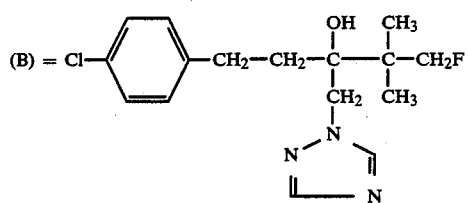

(B) =

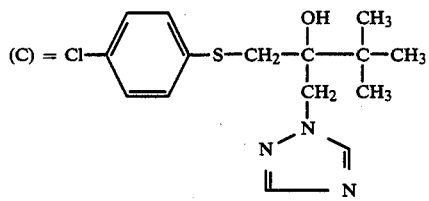

(C) =

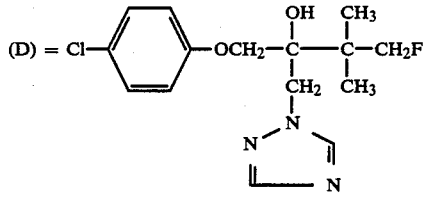

(D) =

Example A
Botrytis test (beans)/protective
Solvent: 4.7 parts by weight of acetone
Emulsifier: 0.3 parts by weight of alkylaryl polyglycol ether To produce a suitable preparation of active compound, 1 part by weight of active compound is mixed with the stated amounts of solvent and emulsifier, and the concentrate is diluted with water to the desired concentration.

To test for protective activity, young plants are sprayed with the preparation of active compound until dripping wet. After the spray coating has dried on, 2 small pieces of agar covered with Botrytis cinerea are placed on each leaf. The inoculated plants are placed in a darkened humid chamber at 20° C. 3 days after the inoculation, the size of the infected spots on the leaves is evaluated.

In this test substances (I-2), (I-43), (I-44), (I-45), (I-50) and (I-68) according to the invention exhibit a better activity than comparison substance (A).

Example B
Leptosphaeria nodorum test (wheat)/protective
Solvent: 100 parts by weight of dimethylformamide
Emulsifier: 0.25 parts by weight of alkylaryl polyglycol ether To produce a suitable preparation of active compound, 1 part by weight of active compound is mixed with the stated amounts of solvent and emulsifier, and the concentrate is diluted with water to the desired concentration.

To test for protective activity, young plants are sprayed with the preparation of active compound until dew-moist. After the spray coating has dried on, the plants are sprayed with a conidia suspension of Leptosphaeria nodorum. The plants remain for 48 hours in an incubation cabin at 20° C. and 100% relative atmospheric humidity.

The plants are placed in a greenhouse at a temperature of about 15° C. and a relative atmospheric humidity of about 80%.

Evaluation is effected 10 days after the inoculation.

In this test, substances (I-2), (I-41), (I-46), (I-47), (I-48), (I-53), (I-54), (I-55), (I-58), (I-59), (I-60), (I-61) and (I-68) according to the invention exhibit a better activity than comparison substance (B).

Example C
Fusarium culmorum test (wheat)/seed treatment
The active compounds are used as dry dressings. These are prepared by extending the particular active compound with a ground mineral to give a finely pulverulent mixture, which ensures uniform distribution on the seed surface.

To apply the dressing, the infected seed is shaken with the dressing in a closed glass flask for 3 minutes.

2 batches of 100 grains of the wheat are sown 1 cm deep in standard soil and are cultivated in a greenhouse at a temperature of about 18° C. in seedboxes which are exposed to light for 15 hours daily.

About 3 weeks after sowing, the plants are evaluated for symptoms.

In this test, active compound (I-46) according to the invention exhibits a better activity than comparison substance (B).

Example D

Test with Psoroptes ovis

Solvent: 35 parts by weight of ethylene glycol monomethyl ether 35 parts by weight of nonylphenol polyglycol ether To produce a suitable preparation of active compound, three parts by weight of active compound are mixed with seven parts by weight of the abovementioned solvent mixture and the concentrate thus obtained is diluted with water to the desired concentration.

About 10-25 Psoroptes ovis are introduced into 1 ml of the active compound preparation to be tested, this having been pipetted into tablet nests of a deep-drawn package. After 24 hours the degree of destruction is determined.

In this test, active compounds (I-41), (I-57) and (I-60) according to the invention exhibit a better activity than comparison substances (C) and (D).

It will be understood that the specification and examples are illustrative but not limitative of the present invention and that other embodiments within the spirit and scope of the invention will suggest themselves to those skilled in the art.

What is claimed is:

1. A mercapto-substituted hydroxyethyl-(triazol-1-yl) compound of the formula

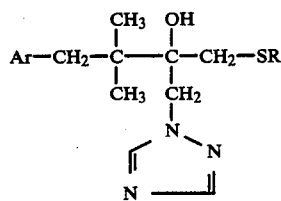

in which

Ar represents phenyl which can be monosubstituted, disubstituted or trisubstituted by identical or different substituents from the group consisting of halogen, alkyl with 1 to 4 carbon atoms, halogenoalkyl with 1 to 2 carbon atoms and 1 to 5 halogen atoms, halogenoalkoxy with 1 or 2 carbon atoms and 1 to 5 halogen atoms, halogenoalkylthio with 1 or 2 carbon atoms and 1 to 5 halogen atoms and phenyl.

R represents hydrogen, straight-chain or branched alkyl with 1 to 12 carbon atoms, alkenyl with 2 to 12 carbon atoms, cycloalkyl which has 3 to 6 carbon atoms, cycloalkylalkyl which has 3 to 6 carbon atoms, in the cycloalkyl part and 1 or 2 carbon atoms in the alkyl part and is optionally monosubstituted or disubstituted by halogen, or represents aralkyl which has 6 to 10 carbon atoms, in the aryl part and 1 to 4 carbon atoms in the alkyl part, it being possible for the aryl part to be substituted by halogen, or R represents phenyl which is mono-, di- or tri-substituted by halogen and/or alkyl with 1 to 4 carbon atoms.

2. A mercapto-substituted hydroxyethyl-(triazol-1-yl) compound as claimed in claim 1, wherein Ar represents phenyl which can be monosubstituted, disubstituted or trisubstituted by identical or different substituents from the group consisting of fluomine, chlorine, bromine, methyl, ethyl, isopropyl, butyl, trifluoromethyl, trifluoromethoxy, tetrafluoroethoxy, trifluoromethylmercapto, tetrafluoroethylmercapto and phenyl, and R represents hydrogen, alkyl which has 1 to 6 carbon atoms, alkenyl which has 2 to 4 carbon atoms, cycloalkyl which has 3 to 6 carbon atoms, cycloalkylalkyl which has 3 to 6 carbon atoms in the cycloalkyl part and 1 to 2 carbon atoms in the alkyl part and is optionally mono- or disubstituted by identical or different substituents from the group consisting of fluorine and chlorine, or represents benzyl, which can be monosubstituted, disubstituted or trisubstituted in the phenyl part by identical or different substituents from the group consisting of fluorine and chlorine, or R represents phenyl which is mono- or disubstituted by fluorine, chlorine or methyl.

3. A mercapto-substituted hydroxyethyl-(triazol-1-yl) compound as claimed in claim 1, wherein Ar represents phenyl, which can be monosubstituted, disubstituted or trisubstituted by identical or different substituents from the group consisting of fluorine, chlorine, bromine, methyl, ethyl, isopropyl, butyl, trifluoromethyl, trifluoromethoxy, tetrafluoroethyoxy, trifluoromethylmercapto, tetrafluoroethylmercapto and phenyl, and R represents hydrogen, alkyl which has 1 to 6 carbon atoms, alkenyl which has 2 to 4 carbon atoms, cycloalkyl which has 3 to 6 carbon atoms, cycloalkylalkyl which has 3 to 6 carbon atoms in the cycloalkyl part and 1 or 2 carbon atoms in the alkyl part and is optionally mono- or disubstituted by identical or different substituents from the group consisting of fluorine and chlorine, or represents benzyl, which can be monosubstituted, disubstituted or trisubstituted in the phenyl part by idential or different substituents from the group consisting of fluroine, chlorine and bromine, or R represents phenyl which is optionally mono- or disubstituted by fluorine, chlorine or methyl.

4. A mercapto-substituted hydroxyethyl-(triazol-1-yl) compound as claimed in claim 1, wherein Ar represent phenyl, which can be monosubstituted or disubstituted by identical or different substituents from the group consisting of fluorine, chlorine, bromine, methyl, ethyl, isopropyl, butyl, trifluoromethyl, trifluoromethoxy, tetrafluoroethoxy, trifluoromethylmercapto, tetrafluoroethylmercapto and phenyl, and R represents hydrogen, methyl, ethyl, isopropyl, n-propyl, n-butyl, iso-butyl, tert.-butyl, n-hexyl, allyl, cyclohexyl, dichlorocyclopropyl-methyl, 4-chlorobenzyl or 4-chlorophenyl.

5. A mercapto-substituted hydroxyethyl-(triazol-1-yl) compound as claimed in claim 1, wherein Ar represents phenyl which can be monosubstituted or disubstituted by identical or different substituents from the group consisting of fluorine, chlorine, bromine, methyl, ethyl, isopropyl, butyl, trifluoromethyl, trifluoromethoxy, tetrafluoroethoxy, trifluoromethylmercapto, tetrafluoroethylmercapto and phenyl, and R represents hydrogen, methyl, ethyl, isopropyl, n-propyl, n-butyl, iso-butyl, tert.-butyl, n-hexyl, allyl, cyclohexyl, dischlorocyclopropyl, dichloroyclopropylmethyl, 4-chlorobenzyl or 4-chlorophenyl.

6. A mercapto-substituted hydroxyethyl-(triazol-1-yl) derivative as claimed in claim 1, designated by the formula

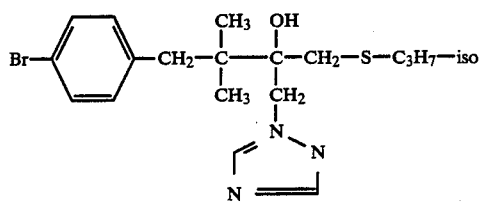

7. A mercapto-substituted hydroxyethyl-(triazol-1-yl) derivative as claimed in claim 1, designated by the formula

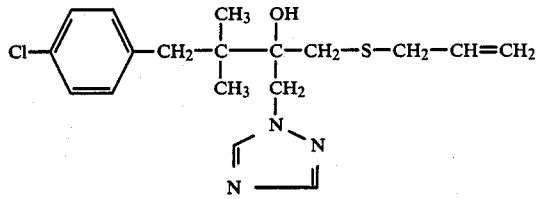

8. A mercapto-substituted hydroxyethyl-(triazol-1-yl) derivative as claimed in claim 1, designated by the formula

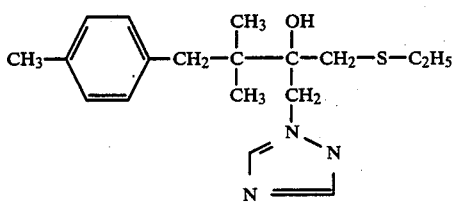

9. A fungicidal composition comprising a fungicidally effective amount of a compound as claimed in claim 1.

10. A method of combating fungi comprising applying to the fungi or to a habitat of such fungi, a fungicidally effective amount of a compound as claimed in claim 1.

* * * * *